US009957249B2

(12) United States Patent
Willand et al.

(10) Patent No.: US 9,957,249 B2
(45) Date of Patent: May 1, 2018

(54) SATURATED NITROGEN AND N-ACYLATED HETEROCYCLES POTENTIATING THE ACTIVITY OF AN ACTIVE ANTIBIOTIC AGAINST *MYCOBACTERIA*

(71) Applicant: Universite de Droit et de la Sante de Lille 2, Lille (FR)

(72) Inventors: Nicolas Willand, Lille (FR); Benoit Deprez, Lille (FR); Alain Baulard, Tournai (BE); Priscille Brodin, Paris (FR); Marion Flipo, Lille (FR); Lucie Maingot, Cambridgeshire (GB)

(73) Assignee: UNIVERSITE DE DROIT ET DE LA SANTE DE LILLE 2, Lille (FR)

( * ) Notice: Subject to any disclaimer, the term of this patent is extended or adjusted under 35 U.S.C. 154(b) by 0 days. days.

(21) Appl. No.: 14/653,669

(22) PCT Filed: Dec. 20, 2013

(86) PCT No.: PCT/EP2013/077732
§ 371 (c)(1),
(2) Date: Jun. 18, 2015

(87) PCT Pub. No.: WO2014/096378
PCT Pub. Date: Jun. 26, 2014

(65) Prior Publication Data
US 2015/0307471 A1    Oct. 29, 2015

(30) Foreign Application Priority Data

Dec. 21, 2012 (FR) ..................... 12 03548

(51) Int. Cl.
| | | |
|---|---|---|
| *C07D 401/04* | (2006.01) | |
| *C07D 295/185* | (2006.01) | |
| *C07D 211/16* | (2006.01) | |
| *C07D 211/18* | (2006.01) | |
| *C07D 211/22* | (2006.01) | |
| *C07D 207/08* | (2006.01) | |
| *A61K 31/40* | (2006.01) | |
| *A61K 31/451* | (2006.01) | |
| *A61K 31/4545* | (2006.01) | |
| *A61K 31/495* | (2006.01) | |
| *A61K 45/06* | (2006.01) | |

(52) U.S. Cl.
CPC ............ *C07D 401/04* (2013.01); *A61K 31/40* (2013.01); *A61K 31/451* (2013.01); *A61K 31/4545* (2013.01); *A61K 31/495* (2013.01); *A61K 45/06* (2013.01); *C07D 207/08* (2013.01); *C07D 211/16* (2013.01); *C07D 211/18* (2013.01); *C07D 211/22* (2013.01); *C07D 295/185* (2013.01)

(58) Field of Classification Search
None
See application file for complete search history.

(56) References Cited

U.S. PATENT DOCUMENTS

| | | |
|---|---|---|
| 4,093,726 A | 6/1978 | Winn et al. |
| 8,338,599 B2 | 12/2012 | Deprez et al. |
| 8,912,329 B2 | 12/2014 | Schoenmakers et al. |
| 8,962,658 B2 | 2/2015 | Deprez et al. |
| 9,050,295 B2 | 6/2015 | Fussenegger et al. |
| 2004/0135117 A1 | 7/2004 | Liu et al. |
| 2011/0319619 A1 | 12/2011 | Nam et al. |

(Continued)

FOREIGN PATENT DOCUMENTS

| | | |
|---|---|---|
| EP | 0120465 A1 | 10/1984 |
| EP | 1118612 A1 | 7/2001 |
| JP | S44-8507 B | 4/1969 |

(Continued)

OTHER PUBLICATIONS

"Tuberculosis (TB) prevention", http://www.webmd.com/lung/tc/tuberculosis-tb-prevention, accessed Oct. 17, 2016.*
"MeSH browser record", https://www.nlm.nih.gov/cgi/mesh/2016/MB_cgi?mode=&index=9186&field=all&HM=., accessed Oct. 17, 2016.*
"Periodic Table", available Dec. 12, 2006.*
"Syphilis-prevention", http://www.webmd.com/sexual-conditions/tc/syphilis-prevention?print=true, accessed Apr. 29, 2010.*
Tripathi. Bioorganic and Medicinal Chemistry, 1999, 9 (18), 2693-98.*
March. Advanced Organic Chemistry,, 1992, 357-62.*
U.S. Appl. No. 14/430,604, Universite de Droit et de la Sante de Lille 2.
Zhang, Z., et al., "Highly Efficient and Practical Phosphoramidite-Copper Catalysts for Animation of Aryl Iodides and Heteroaryl Bromides with Alkylamines and N(H)-Heterocycles," *Tetrahedron* 62: 4435-4443 (2006), Elsevier.

(Continued)

*Primary Examiner* — Noble E Jarrell
(74) *Attorney, Agent, or Firm* — Cynthia M. Bouchez; Medler Ferro Woodhouse & Mills PLLC

(57) ABSTRACT

The present invention concerns a compound of general formula (I):

(I)

in which n=0 or 1, R1 represents an optionally substituted alkyl chain, in particular substituted alkyl chain, in particular substituted with fluorine, X is chosen from N and CH, and R2 is chosen from optionally substituted phenyl and benzyl, wherein the heterocycles having 6 vertices comprise one, two or three nitrogen atoms. The present invention also concerns the use of this compound as a medicament, in particular in the treatment of bacterial and mycobacterial infections such as tuberculosis in combination with an antibiotic that is active against bacteria and/or mycobacteria, said compound potentiating the activity of said antibiotic.

20 Claims, No Drawings

(56) References Cited

U.S. PATENT DOCUMENTS

2014/0031391 A1    1/2014    Hahn et al.

FOREIGN PATENT DOCUMENTS

| WO | 2007092681 | * | 8/2007 | |
| WO | WO 2008/003861 | | 1/2008 | |
| WO | 2009077527 | * | 6/2009 | |
| WO | WO 2010/005783 | | 1/2010 | |
| WO | WO 2010/044885 | | 4/2010 | |
| WO | WO 2010/063774 | | 6/2010 | |
| WO | WO 2010/149761 A1 | | 12/2010 | |
| WO | 2013170113 | * | 11/2013 | ........... C07D 401/14 |
| WO | WO 2014/096369 | | 6/2014 | |

OTHER PUBLICATIONS

Irikura, T., et al., "New Analgetic Agents V. 1-Butyryl-4-cinnamylpiperazine Hydrochloride and Related Compounds," *Journal of Medicinal Chemistry 11*: 801-804 (1968).

Flipo, M., et al., "Ethionamide Boosters: Synthesis, Biological Activity, and Structure-Activity Relationships of a Series of 1,2,4-Oxadiazole EthR Inhibitors," *Journal of Medicinal Chemistry 54*: 2994-3010, The American Chemical Society (2011).

Flipo, M., et al., "Ethionamide Boosters. 2. Combining Bioisosteric Replacement and Structure-Based Drug Design to Solve Pharmacokinetic Issues in a Series of Potent 1,2,4-Oxadiazole EthR Inhibitors," *Journal of Medicinal Chemistry 55*: 68-83, The American Chemical Society (2011).

Li, G., et al., "Design and Synthesis of 4-Arylpiperidinyl Amide and N-Arylpiperdin-3-yl-Cyclopropane Carboxamide Derivatives as Novel Melatonin Receptor Ligands," *Bioorganic & Medical Chemistry Letters 21*: 1236-1242 (2011), Elsevier.

Baulard, A., et al., "Activation of the Pro-drug Ethionamide Is Regulated in Mycobacteria," *J. Biol. Chem. 275*: 28326-28331 (2000).

CAS No. 77251-50-4, retrieved from the STN Registry Data Base on Feb. 14, 2017.

Brown et al., *Journal of Medicinal Chemistry* 51:7806-7819, published online Nov. 18, 2008.

Rehse et al., *Archiv der Pharmazie* 312:670-681, 1979 (abstract in English).

STN Database Registry No. 1197686-35-3, entered into STN Dec. 16, 2009.

STN Database Registry No. 1183501-13-4, entered into STN Sep. 13, 2009.

STN Database Registry No. 1147413-58-8, entered into STN May 19, 2009.

STN Database Registry No. 1089559-88-5, entered into STN Dec. 24, 2008.

STN Database Registry No. 1311681-60-3, entered into STN Jul. 7, 2011.

STN Database Registry No. 1178162-16-7, entered into STN Aug. 30, 2009.

Gooding et al., *Journal of Combinatorial Chemistry* 4(6):576-583 (2002).

Caterina et al., *Heterocycles* 78(3):771-781 (2009).

STN Database Registry No. 1390304-42-3, entered into STN Aug. 13, 2012.

STN Database Registry No. 1241539-94-5, entered into STN Sep. 16, 2010.

STN Database Registry No. 1216896-56-8, entered into STN Apr. 5, 2010.

STN Database Registry No. 1215790-81-0, entered into STN Apr. 2, 2010.

STN Database Registry No. 1210750-14-3, entered into STN Mar. 17, 2010.

STN Database Registry No. 1210535-85-5, entered into STN Mar. 16, 2010.

STN Database Registry No. 1209679-19-5, entered into STN Mar. 14, 2010.

STN Database Registry No. 1209411-55-1, entered into STN Mar. 12, 2010.

STN Database Registry No. 1209130-77-7, entered into STN Mar. 12, 2010.

STN Database Registry No. 1011617-04-1, entered into STN Apr. 2, 2008.

STN Database Registry No. 1011572-39-6, entered into STN Apr. 2, 2008.

STN Database Registry No. 1007670-01-0, entered into STN Mar. 13, 2008.

STN Database Registry No. 544679-20-1, entered into STN Jul. 9, 2003.

STN Database Registry No. 543722-88-9, entered into STN Jul. 7, 2003.

STN Database Registry No. 349416-47-3, entered into STN Jul. 29, 2001.

STN Database Registry No. 349416-45-1, entered into STN Jul. 29, 2001.

STN Database Registry No. 347909-31-3, entered into STN Jul. 24, 2001.

* cited by examiner

SATURATED NITROGEN AND N-ACYLATED HETEROCYCLES POTENTIATING THE ACTIVITY OF AN ACTIVE ANTIBIOTIC AGAINST *MYCOBACTERIA*

The present invention relates to a compound for use in the treatment of bacterial and mycobacterial infections, such as for example tuberculosis, leprosy and atypical mycobacterial infections.

The present invention also concerns new compounds that can be used as medicament, in particular as medicament in the treatment of bacterial and mycobacterial infections such as, for example, tuberculosis, leprosy and atypical mycobacterial infections.

The present invention also concerns pharmaceutical compositions comprising, as the active ingredient, at least one of the abovementioned compounds and optionally an antibiotic active against bacteria and/or mycobacteria, notably an antibiotic activatable via the EthA pathway, more particularly an antibiotic chosen from the family of thioamides, for example ethionamide or prothionamide.

The present invention also concerns products (kits) containing at least one of the aforementioned compounds and at least one antibiotic active against bacteria and/or mycobacteria, notably an antibiotic activatable via the EthA pathway, more particularly an antibiotic chosen from the family of thioamides, for example ethionamide or prothionamide, as combination products for use simultaneously, separately or spread out in time, in the therapy of tuberculosis, leprosy or general mycobacterial infections Tuberculosis kills 2 million people every year in the world. The AIDS epidemics and the emergence of strains that are multi-resistant to antibiotics contribute to exacerbating the impact of this illness, considered by the World Health Organization as responsible for an increasingly dangerous worldwide epidemic and as a health emergency on a global scale.

An increasing number of *Mycobacterium tuberculosis* strains is characterized nowadays by multi-resistance to first-line antibiotics such as isoniazid (INH) and rifampicin (RIF). These antibiotics must then be replaced by second-line antibiotics such as ethionamide (ETH) to which the strains are not resistant but which have the disadvantage of having a low therapeutic index (the therapeutic index of an active ingredient is the ratio of therapeutic dose to toxic dose).

One strategy consisting in increasing the activity of ethionamide (ETH) by associating it to a specific compound has already been considered. In fact, ETH is a prodrug that is transformed in vivo into a therapeutically active form by the EthA enzyme (see the article "Activation of the prodrug ethionamide is regulated in mycobacteria", A. R. Baulard et al., Journal of Biological Chemistry, 2000, 275, 28326-28331). The observed resistances to ETH arise from the fact that the transcriptional repressor EthR of *M. tuberculosis* controls the expression of the EthA enzyme and restricts the transformation of ETH into a therapeutically active substance.

One aim of the present invention is to propose new compounds likely to potentiate notably the activity of antibiotics active against tuberculosis, in particular an antibiotic chosen from the thioamide family, such as ethionamide or prothionamide for example.

Another aim of the present invention is to propose compounds such as previously mentioned that, in combination with an antibiotic active against tuberculosis, chosen from the thioamide family, in particular ethionamide and/or prothionamide, and at identical antibiotics dosage, enable a greater efficiency to be achieved or that enable the aforementioned antibiotics dosage to be reduced to achieve a given efficiency.

Another aim of the present invention is to propose compounds such as previously mentioned that are simple and inexpensive to produce.

Another aim of the present invention is to propose compounds such as previously mentioned that are satisfactorily soluble in a biologic fluid.

Another aim of the present invention is to propose compounds such as previously mentioned that are likely to be active in particular orally and/or that cause fewer side effects.

To achieve at least one of the aforementioned aims, the present invention thus proposes compounds of the general formula (I):

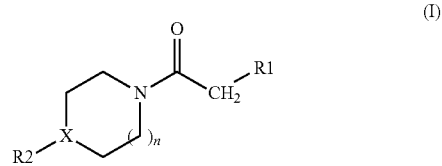

in which:
n=0 or 1;
R1 represents a group chosen from:
linear or branched and optionally substituted C1-C5 alkyl chains;
  in particular substituted by at least one fluorine atom (F), linear or branched C1-C3 alkyl chains substituted by at least one fluorine atom (F) or by a C3-C6 saturated or unsaturated cyclic group; and
the groups $CH_2CF_3$, $(CH_2)_2CF_3$, $CF_2CF_3$;
X is chosen from N and CH;
R2 is chosen from the following groups: phenyl, benzyl, phenyl or benzyl groups substituted by at least one linear or branched C1-C4 alkyl chain, phenyl or benzyl groups substituted by at least one linear or branched and substituted C1-C4 alkyl chains, in particular substituted by at least one fluorine atom (F), phenyl groups substituted by at least one group chosen from Cl, F, $CF_3$, $OCH_3$ or OH, and the heterocycles having 6 vertices, saturated or unsaturated, comprising one, two or three nitrogen atoms.

Advantageously, m=n=1. Such components in combination with ethionamide prove particularly active on mycobacteria, in particular on *M. tuberculosis*.

R1 can be chosen from the following groups: —$CH_2$-isopropyl; cyclopropyl, cyclobutyl, cyclopentyl, —$CH_2$-cyclopropyl, —$CH_2$-cyclobutyl, and —$CH_2$-cyclopentyl.

Advantageously, R1 is a —$CH_2CF_3$ group. Such components exhibit a good potentiating activity of ethionamide, in particular on *M. tuberculosis*.

Advantageously, X=CH. Such components have proven more efficient in combination with ethionamide, in particular on the bacterium *M. tuberculosis*.

According to a first embodiment, R2 is a phenyl group.
According to a second embodiment, R2 is a benzyl group.
According to a third embodiment, R2 is a phenyl group substituted by at least one F atom.
According to a fourth embodiment, R2 is a phenyl group substituted in meta position relative to the bonding to X, by Cl, F, $CF_3$ or $CH_3$.

Advantageously, R2 is a phenyl group substituted in para position relative to its bonding to X by a fluorine atom F.
According to another embodiment, R2 is a group chosen from the following groups:
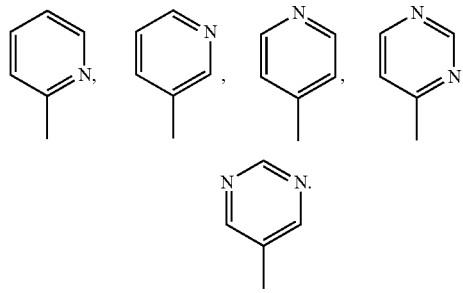
The inventive compound can be chosen from the following compounds:
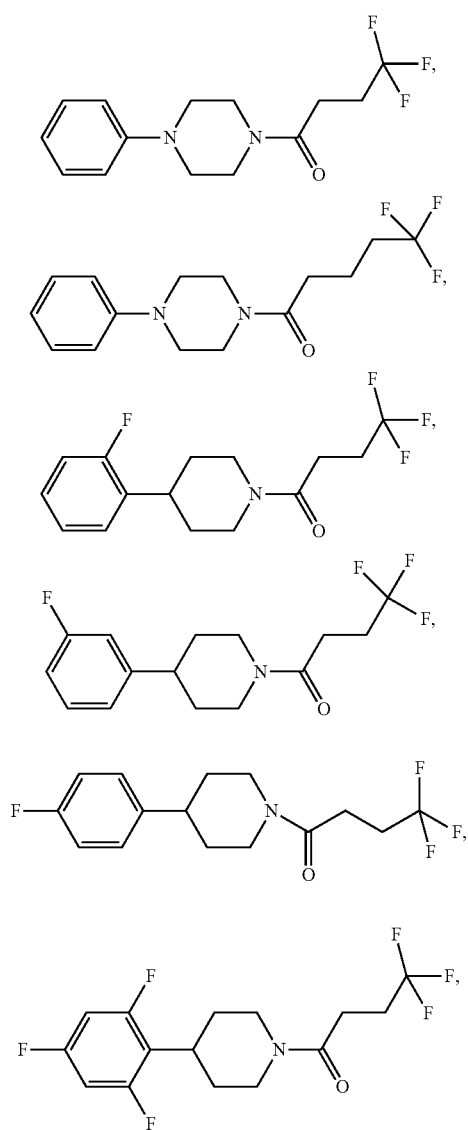
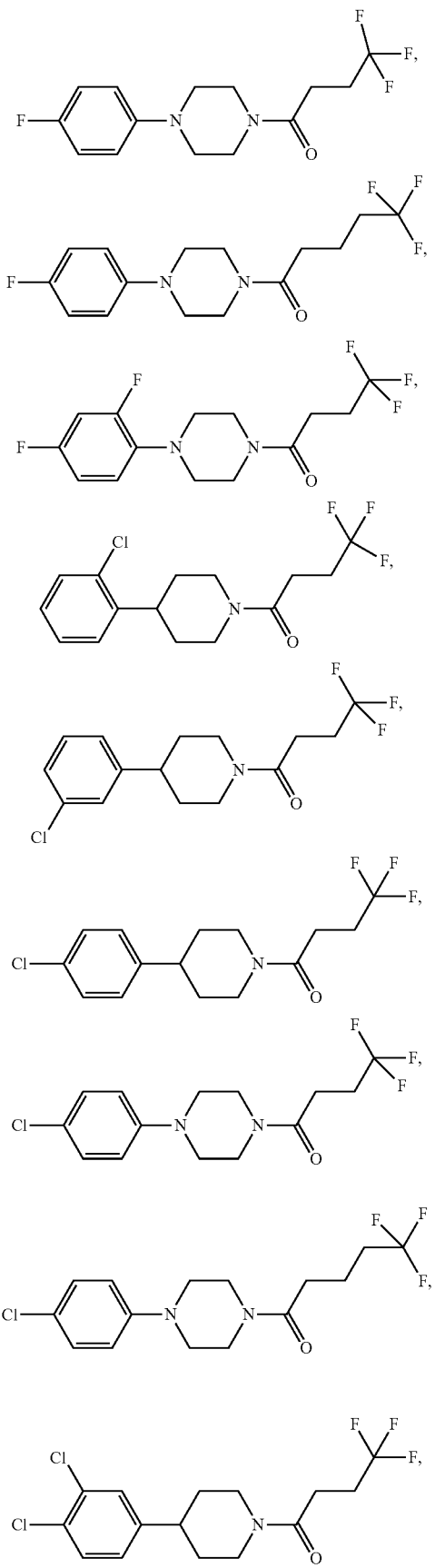

-continued
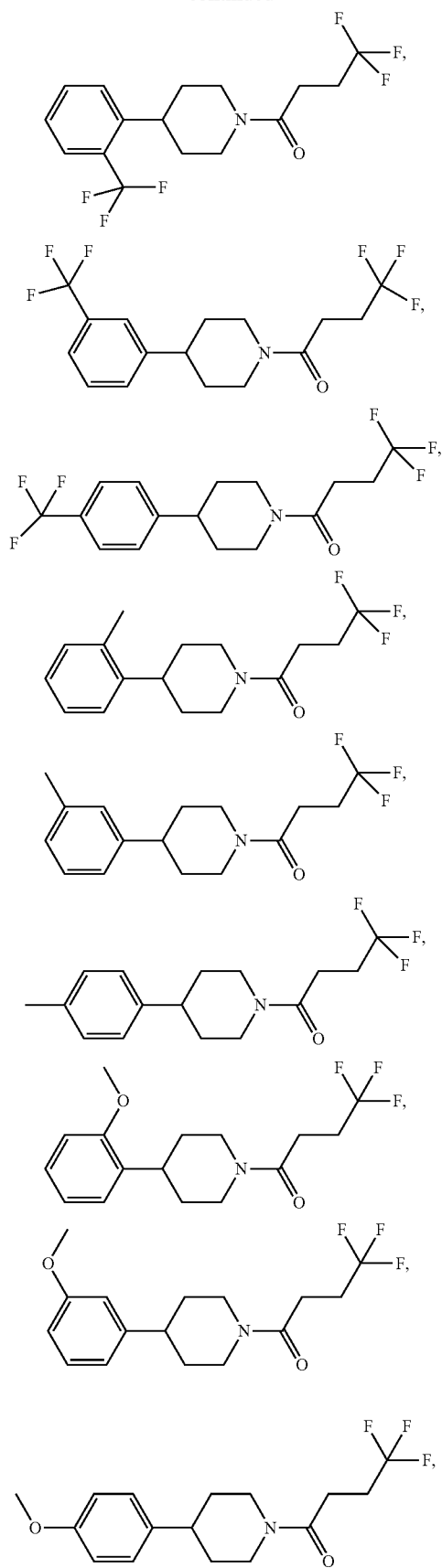
-continued
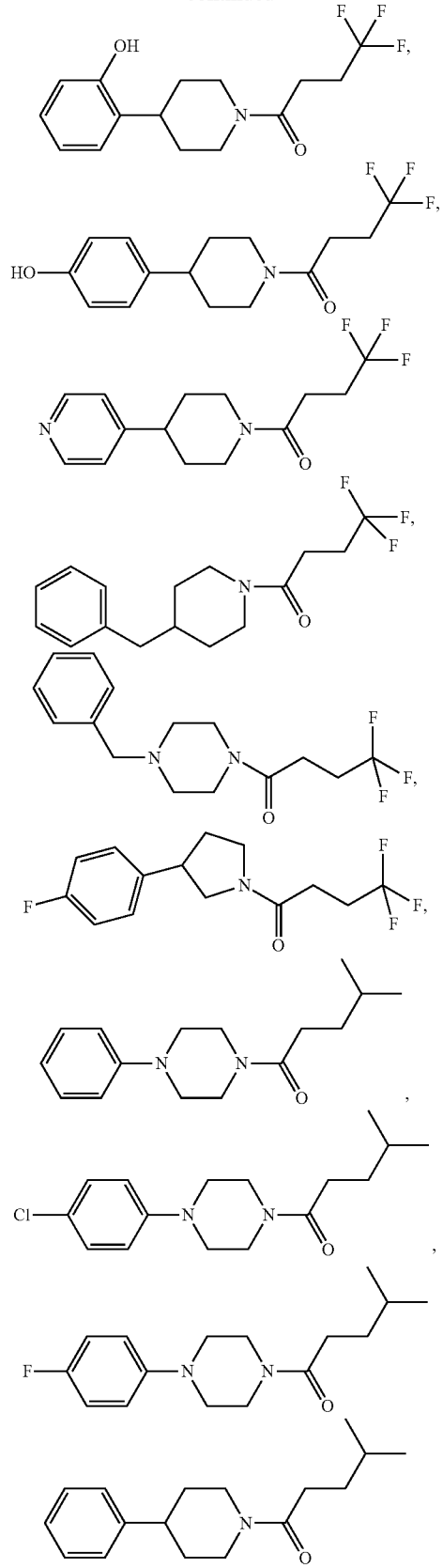
The present invention also concerns the aforementioned compound for its use as medicament, in particular for its use in the treatment of bacterial and mycobacterial infections, notably in the treatment of tuberculosis, leprosy or atypical mycobacterial infections.

The present invention also concerns a pharmaceutical composition comprising, as the active ingredient, at least one compound of general formula (I) as previously mentioned and one pharmaceutically acceptable excipient.

Within the pharmaceutical compositions according to the invention, the compound or compounds used as active ingredient(s) can be used in a quantity that enables unit doses comprised between 0.3 mg and 1 g approximately to be administered. Within the pharmaceutical compositions according to the invention, the antibiotic or antibiotics active against mycobacteria are, when present, advantageously used in a quantity enabling the administration of unit doses equal to or lower than the doses usually recommended by the World Health Organization (WHO, Treatment of tuberculosis: Guidelines for National Programs. 2003; WHO/CDS/TB2003.313), national or non-governmental health organizations or the competent pharmaceutical laboratories.

The one skilled in the art is able to choose one or several pharmaceutically acceptable excipients depending on the route of administration of the pharmaceutical composition. The one skilled in the art will of course ensure in doing so that the excipient or excipients used are compatible with the intrinsic properties attached to the composition according to the present invention. Furthermore, the form of the medicament or pharmaceutical composition (for example a solution, a suspension, an emulsion, tablets, capsules, suppositories etc.) will depend on the chosen administration route.

Thus, in the sense of the present invention, the medicament or pharmaceutical composition can be administered by any appropriate route, for example oral, anal, local (topical for example), systemic, intravenous, intramuscular or mucosal route, or else by using a patch, or else in encapsulated form in or immobilized on liposomes, microparticles, microcapsules, associated to nanoparticles and similar. By way of non-limiting examples of excipients suitable for administration by the oral route, one can notably cite talcum, lactose, starch and its derivatives, cellulose and its derivatives, polyethylene glycols, acrylic acid polymers, gelatin, magnesium stearate, animal, vegetal or synthetic fats, paraffin derivatives, glycols, stabilizers, preservatives, antioxidants, wetting agents, anti-caking agents, dispersants, emulsifiers, taste modifying agents, penetrating agents, solubilizing agents etc. The formulation and administration techniques for the medicaments and pharmaceutical compositions are well known in the art here under consideration, the one skilled in the art can notably refer to the work Remington's Pharmaceutical Sciences, latest edition.

The present invention also has the aim of using at least one compound according to the invention for the manufacture of a medicament intended for the prevention and/or treatment of bacterial infections, preferably mycobacterial infections, and more particularly of tuberculosis, leprosy or atypical mycobacterial infections.

Advantageously, the pharmaceutical composition further comprises, as active ingredient, at least one antibiotic active against bacteria and/or mycobacteria, in particular an antibiotic activatable via the EthA pathway, more particularly an antibiotic chosen notably from the thioamide family, in particular from ethionamide and prothionamide.

However, the invention is not limited to these antibiotics. The inventive compounds prove to be compounds potentiating antibiotics activatable via the EthA pathway; however, the inventive compounds can also be used as potentiating agents of the antibiotic activity of antibiotics that can be bio-activated via another bio-activation pathway or pathways than the aforementioned one.

The present invention also concerns a kit or product containing at least one compound of formula (I) and at least one antibiotic active against bacteria and/or mycobacteria in particular, in particular an antibiotic activatable via the enzymatic EthA pathway, more particularly an antibiotic chosen from the thioamide family, in particular chosen from ethionamide and prothionamide as combination products for use, simultaneously, separately or spread out in time, in the therapy of tuberculosis, leprosy or general mycobacterial infections.

Definitions

Within the whole of the present application, when it is not indicated that a group, whatever it is, is substituted, the latter is not substituted.

Within the meaning of the present invention, a substituted phenyl group is defined as a mono-, di- or tri-substituted phenyl group. The position of the substituent or substituents, when it is not indicated, is not limited according to the invention. When the substituent or substituents are indicated, the phenyl group can also comprise one or several other substituents different from those mentioned.

Preferably, the phenyl groups substituted by Cl, $CF_3$, and $CH_3$ are mono-substituted and the substituent (Cl, $CF_3$ or $CH_3$) is preferably in meta position relative to the carbon of the benzene cycle bound to X. Preferably, X is CH.

In the case of a phenyl group substituted by a fluorine atom, all the groups mono-, di- or tri-substituted by fluorine atoms are included in the present invention. Advantageously, the phenyl groups substituted by one or several fluorine atoms are not substituted by another group or by another atom other than F. Thus, phenyl groups substituted by at least one fluorine atom include, within the meaning of the present invention, phenyl groups mono-substituted by a fluorine atom, situated in ortho, meta or para position of the carbon of the benzene cycle bound to X, phenyl groups substituted by two fluorine atoms, in particular phenyl groups substituted by two fluorine atoms placed in ortho and para position of the bond of the benzene cycle with X, phenyl groups having three carbon atoms substituted each by a fluorine atom, in particular a phenyl group tri-substituted by three fluorine atoms of which two fluorine atoms are in ortho position of the bond of the benzene cycle with X and one fluorine atom is in para position relative to this bond.

Atypical mycobacterial infections are defined here as mycobacterial infections caused by at least one *mycobacterium* other than *M. Tuberculinum* and in particular mycobacterial infections involving M. *Kansasii*.

According to the present invention, the term "treatment" designates the curative treatment and/or prophylactic treatment of the aforementioned infections. The term "treatment" includes all improvement of the patient's state, in particular any diminution of the number of bacteria present in at least one infection site of the patient.

Within the meaning of the present invention, an antibiotic active against bacteria and/or mycobacteria is defined as any agent capable of limiting or reducing at least in vitro the proliferation of a bacterium and/or of a *mycobacterium*, in particular *M. tuberculosis*. An agent capable of destroying, at least in vitro, a *mycobacterium*, notably *M. tuberculosis*, is also an antibiotic active against mycobacteria within the meaning of the present invention. Among the antibiotics active against mycobacteria and activatable via the enzymatic EthA pathway, ethionamide, prothionamide, isoxyl, thiacetazone and the mixtures of at least two of these antibiotics can be mentioned.

In the present invention, an antibiotic activatable via the EthA pathway is defined as any substance that at least in vitro reacts with the EthA enzyme to produce a substance having antibiotic properties. The one skilled in the art is able to determine if an antibiotic is activatable by the EthA pathway for example by applying the method described in the following publication: "Activation of the prodrug ethionamide is regulated in mycobacteria" A. R. Baulard et al., Journal of Biological Chemistry, 2000, 275, 28326-28331.

The antibiotic within the meaning of the present invention can also be an antibiotic activatable via another bio-activation pathway than the aforementioned one.

EXPERIMENTAL SECTION

Synthesis Process(es)

Nuclear magnetic resonance spectra (NMR)$^1$H and $^{13}$C were performed at ambient temperature on a Bruker™ DPX 300 spectrometer at 300 MHz. The chemical shifts are expressed in parts per million (ppm). The assignments were performed using $^1$H and $^{13}$C one-dimensional (1D) or two-dimensional (2D) HSQC-COSY experiments. Mass spectra were performed on an LCMS Waters Alliance Micromass ZQ 2000 system. The commercial reagents and solvents were used without ulterior purification.

General Flow Diagram of the Synthetic Process(es) for Piperidino and Pyrrolidino Derivatives:

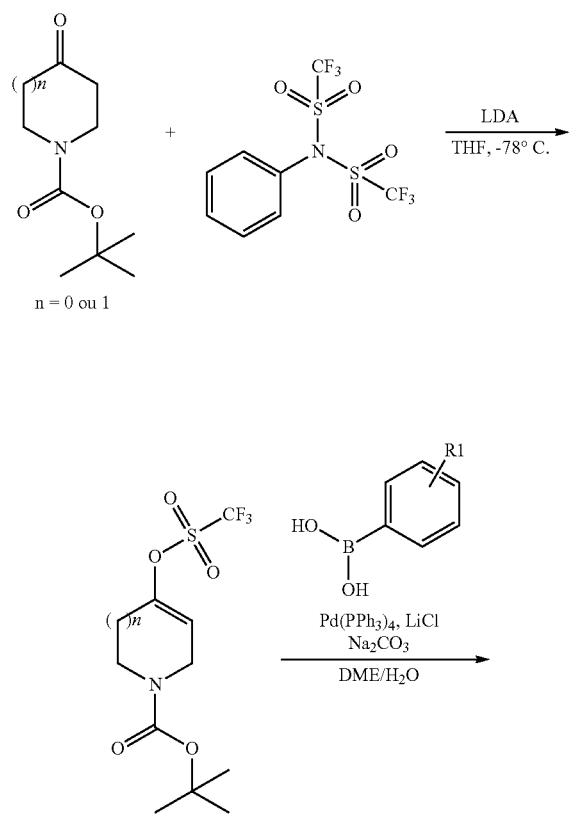

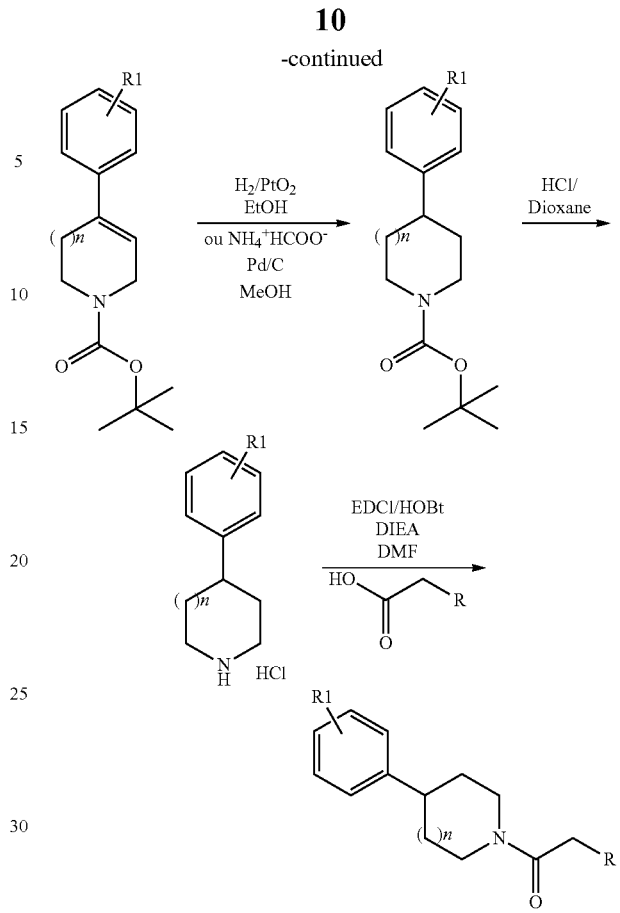

Protocol:

The LDA (solution at 2M in THF/heptane/ethyl benzene, 3.3 mmole 1.1 eq) was added with 5 mL anhydrous THF in a flask previously oven-dried and put under argon. The solution was cooled to −78° C. The N-Boc-4-piperidone (or N-Boc-3-pyrrolidinone) (3 mmol, 1 eq) dissolved in 5 mL THF was added drop-wise, then the reaction medium was agitated for 20 minutes at −78° C. The N-phenyl-trifluoromethane-sulphonimide (3.3 mmol, 1.1 eq) dissolved in 5 mL THF was added. The solution was agitated 2 h at 0° C. and then evaporated. The residue was dissolved in a mixture of cyclohexane/AcOEt 9:1 and then filtrated on alumina. The product (triflate) was used in the next step without purification. In a flask containing the triflate (1 eq) and put under argon, one added the boronic acid (1.1 eq), LiCl (3 eq), the 2N solution of Na$_2$CO$_3$ (1.4 eq), the DME (0.34 M) and the tetrakis(triphenylphosphine)palladium (0.05 eq). The solution was heated between 1 h and 16 h under reflux and then evaporated. The residue was taken up in AcOEt and then washed once using water and once using a solution saturated with NaCl. The organic phase was dried and then evaporated. The residue was taken up in AcOEt and then filtrated on sintered glass. The solvent was evaporated, then the product was purified using chromatography on silica gel (cyclohexane/AcOEt).

The unsaturated derivative (1 eq) was dissolved in ethanol (0.1M) with PtO$_2$ (0.1 eq) or Pd/C (0.1 eq). The reaction mixture was put under hydrogen and agitated at ambient temperature until the input product has disappeared. The solution was filtrated on celite, then evaporated.

Or: the unsaturated derivative (1 eq) was dissolved in methanol (0.1M) with ammonium formate (5 eq) and Pd/C (10% by mass). The reaction mixture was heated under reflux until the input product disappeared. The solution was filtrated on celite and then evaporated.

The protected amine (1 eq.) was added in a flask with dioxane (1 M), then a solution of HCl 4N in dioxane (5 eq) was added. The solution was agitated 1 h at ambient temperature, then evaporated. The residue was taken over in light petroleum and then filtrated on sintered glass.

The acid (1.3 eq) was activated using EDCl (1.3 eq) and HOBt (0.4 eq) in DMF (0.25 M) in the presence of DEIA (4 eq) and then the amine (1 eq) was added. The solution was agitated 3 h at ambient temperature and then evaporated. The residue was dissolved in AcOEt and then washed twice using saturated NaHCO$_3$, twice using HCl 1N and once using saturated NaCl. The organic phase was dried on MgSO$_4$ and then evaporated. The residue was purified using preparative HPLC.

General Flow Diagram of the Synthetic Process(es) for Piperazines:

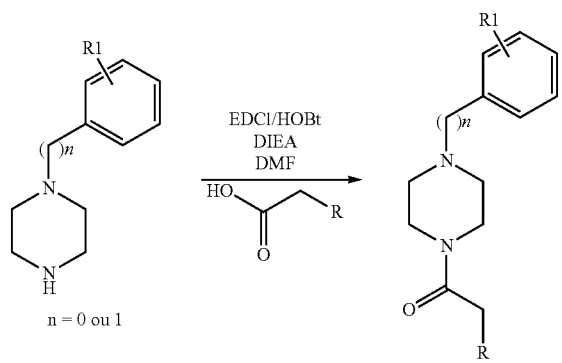

Protocol:

The acid (1.3 eq) was activated using EDCl (1.3 eq) and HOBt (0.4 eq) in DMF (0.25 M) in the presence of DIEA (4 eq), then the commercially available piperazine (1 eq) was added. The solution was agitated 3 h at ambient temperature, then evaporated. The residue was dissolved in AcOEt, then washed twice using saturated NaHCO$_3$, twice using HCl 1N and once using saturated NaCl. The organic phase was dried on MgSO$_4$ then evaporated. The residue was purified using preparative HPLC.

BDM_44647

4-phenylpiperidine is commercially available. Only the coupling was performed.

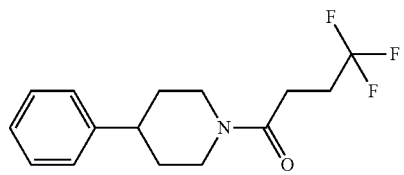

$^1$H NMR (CD$_2$Cl$_2$) δ 7.36-7.31 (m, 2H), 7.25-7.21 (m, 3H), 4.78-4.71 (m, 1H), 3.99-3.93 (m, 1H), 3.22-3.12 (m, 1H), 2.84-2.48 (m, 6H), 1.96-1.86 (m, 2H), 1.72-1.56 (m, 2H). MS [M+H]$^+$ m/z 286.

BDM_44648

4-phenylpiperidine is commercially available. Only the coupling was performed.

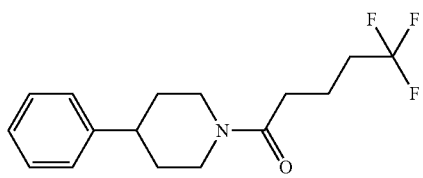

$^1$H NMR (CD$_2$Cl$_2$) δ 7.36-7.31 (m, 2H), 7.25-7.20 (m, 3H), 4.78-4.72 (m, 1H), 3.99-3.92 (m, 1H), 3.19-3.09 (m, 1H), 2.81-2.60 (m, 2H), 2.45 (t, J=7.0 Hz, 2H), 2.29-2.16 (m, 2H), 1.97-1.87 (m, 4H), 1.70-1.54 (m, 2H). MS [M+H]$^+$ m/z 300.

BDM_44808

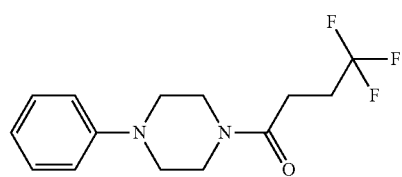 [SMILES: O=C(CCC(F)(F)F)N1CCC(c2ccccc2)CC1]

$^1$H NMR (CDCl$_3$) δ 7.34-7.28 (m, 2H), 6.97-6.94 (m, 3H), 3.83-3.80 (m, 2H), 3.67-3.64 (m, 2H), 3.24-3.17 (m, 4H), 2.68-2.49 (m, 4H). MS [M+H]$^+$ m/z 287.

BDM_44809

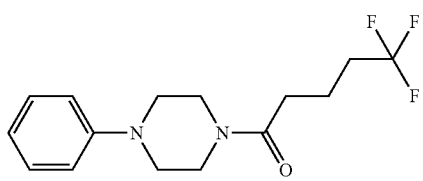 [SMILES: O=C(CCCC(F)(F)F)N1CCN(c2ccccc2)CC1]

$^1$H NMR (CDCl$_3$) δ 7.34-7.28 (m, 2H), 6.97-6.94 (m, 3H), 3.82-3.79 (m, 2H), 3.65-3.62 (m, 2H), 3.22-3.16 (m, 4H), 2.48 (t, J=7.2 Hz, 2H), 2.31-2.15 (m, 2H), 2.03-1.92 (m, 2H). MS [M+H]$^+$ m/z 301.

BDM_70666

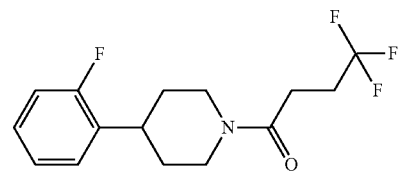 [SMILES: O=C(CCC(F)(F)F)N1CCC(c2ccccc2F)CC1]

$^1$H NMR (CD$_2$Cl$_2$) δ 7.27-7.20 (m, 2H), 7.16-7.03 (m, 2H), 4.79-4.73 (m, 1H), 3.98-3.93 (m, 1H), 3.24-3.08 (m, 2H), 2.74-2.48 (m, 5H), 1.95-1.86 (m, 2H), 1.74-1.63 (m, 2H). MS [M+H]$^+$ m/z 304.

BDM_70531

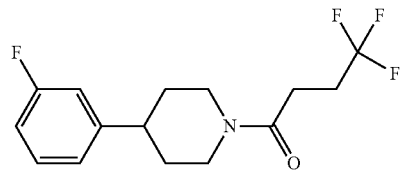 [SMILES: O=C(CCC(F)(F)F)N1CCC(c2cccc(F)c2)CC1]

$^1$H NMR (CD$_2$Cl$_2$) δ 7.27-7.20 (m, 2H), 7.16-7.02 (m, 2H), 4.79-4.74 (m, 1H), 3.99-3.94 (m, 1H), 3.24-3.09 (m, 2H), 2.75-2.49 (m, 5H), 1.95-1.86 (m, 2H), 1.75-1.59 (m, 2H). MS [M+H]$^+$ m/z 304.
BDM_44751

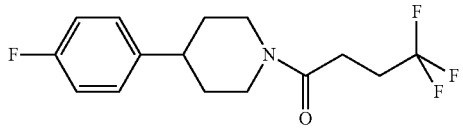 [SMILES: O=C(CCC(F)(F)F)N1CCC(c2ccc(F)cc2)CC1]

$^1$H NMR (CD$_2$Cl$_2$) δ 7.33-7.19 (m, 2H), 7.06-7.00 (m, 2H), 4.77-4.72 (m, 1H), 3.98-3.92 (m, 1H), 3.21-3.11 (m, 1H), 2.83-2.49 (m, 6H), 1.94-1.86 (m, 2H), 1.68-1.46 (m, 2H).

$^{13}$C NMR (CD$_2$Cl$_2$) δ 167.64, 161.45 (d, J=244 Hz), 141.20, 127.42 (q, J=274 Hz), 128.16 (d, J=8 Hz), 115.11 (d, J=21 Hz), 45.83, 42.40, 41.91, 33.81, 32.96, 29.53 (q, J=29 Hz), 25.79. MS [M+H]$^+$ m/z 304.
BDM_71148

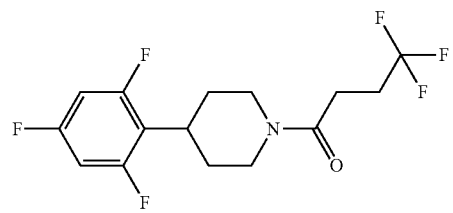 [SMILES: O=C(CCC(F)(F)F)N1CCC(c2c(F)cc(F)cc2F)CC1]

$^1$H NMR (CD$_2$Cl$_2$) δ 6.69 (t, J=8.7 Hz, 2H), 4.78-4.72 (m, 1H), 3.98-3.92 (m, 1H), 3.27-3.10 (m, 2H), 2.68-2.48 (m, 5H), 2.07-1.90 (m, 2H), 1.82-1.74 (m, 2H). MS [M+H]$^+$ m/z 340.
BDM_44819

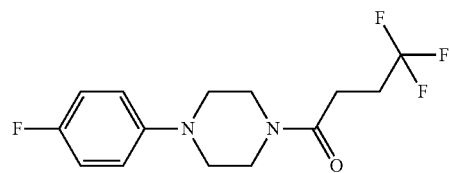 [SMILES: O=C(CCC(F)(F)F)N1CCN(c2ccc(F)cc2)CC1]

$^1$H NMR (CD$_2$Cl$_2$) δ 7.04-6.98 (m, 2H), 6.95-6.90 (m, 2H), 3.79-3.75 (m, 2H), 3.64-3.61 (m, 2H), 3.14-3.07 (m, 4H), 2.61-2.46 (m, 4H). MS [M+H]$^+$ m/z 305.
BDM_44820

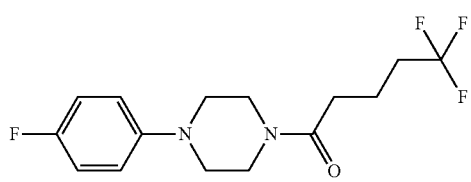 [SMILES: O=C(CCCC(F)(F)F)N1CCN(c2ccc(F)cc2)CC1]

$^1$H NMR (CD$_2$Cl$_2$) δ 7.04-6.98 (m, 2H), 6.94-6.89 (m, 2H), 3.77-3.74 (m, 2H), 3.62-3.59 (m, 2H), 3.12-3.06 (m, 4H), 2.45 (t, J=7.2 Hz, 2H), 2.25-2.15 (m, 2H), 1.97-1.87 (m, 2H). MS [M+H]$^+$ m/z 319.
BDM_70669

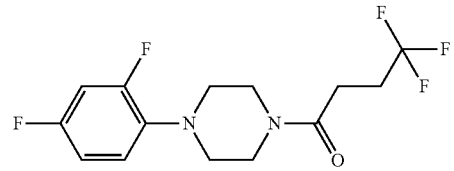 [SMILES: O=C(CCC(F)(F)F)N1CCN(c2ccc(F)cc2F)CC1]

$^1$H NMR (CD$_2$Cl$_2$) δ 6.99-6.82 (m, 3H), 3.79-3.76 (m, 2H), 3.64-3.61 (m, 2H), 3.05-2.99 (m, 4H), 2.67-2.48 (m, 4H). MS [M+H]$^+$ m/z 323.
BDM_70534

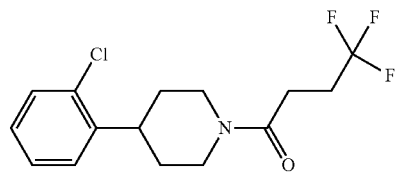 [SMILES: O=C(CCC(F)(F)F)N1CCC(c2ccccc2Cl)CC1]

$^1$H NMR (CD$_2$Cl$_2$) δ 7.41-7.39 (m, 1H), 7.32-7.17 (m, 3H), 4.80-4.75 (m, 1H), 3.99-3.94 (m, 1H), 3.35-3.17 (m, 2H), 2.76-2.49 (m, 5H), 1.99-1.89 (m, 2H), 1.66-1.53 (m, 2H). MS [M+H]$^+$ m/z 320.
BDM_70668

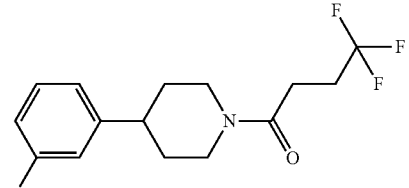

$^1$H NMR (CD$_2$Cl$_2$) δ 7.32-7.21 (m, 3H), 7.15-7.13 (m, 1H), 4.78-4.72 (m, 1H), 3.98-3.93 (m, 1H), 3.21-3.11 (m, 1H), 2.83-2.48 (m, 6H), 1.95-1.87 (m, 2H), 1.69-1.52 (m, 2H). MS [M+H]$^+$ m/z 320.
BDM_70535

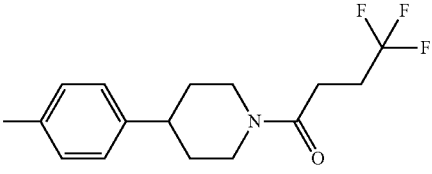

$^1$H NMR (CD$_2$Cl$_2$) δ 7.33-7.30 (m, 2H), 7.20-7.17 (m, 2H), 4.78-4.71 (m, 1H), 3.99-3.92 (m, 1H), 3.21-3.11 (m, 1H), 2.82-2.48 (m, 6H), 1.94-1.86 (m, 2H), 1.67-1.51 (m, 2H). MS [M+H]$^+$ m/z 320.
BDM_44811

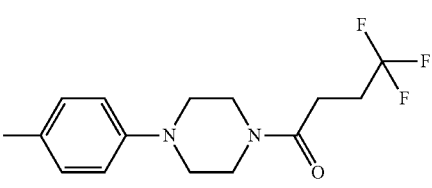

¹H NMR (CD₂Cl₂) δ 7.28-7.23 (m, 2H), 6.91-6.86 (m, 2H), 3.78-3.75 (m, 2H), 3.64-3.61 (m, 2H), 3.20-3.13 (m, 4H), 2.67-2.46 (m, 4H). MS [M+H]⁺ m/z 321.
BDM_44812

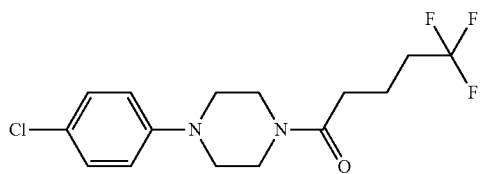 [SMILES: O=C(CCCC(F)(F)F)N1CCN(c2ccc(Cl)cc2)CC1]

¹H NMR (CD₂Cl₂) δ 7.27-7.22 (m, 2H), 6.91-6.86 (m, 2H), 3.77-3.74 (m, 2H), 3.62-3.59 (m, 2H), 3.18-3.12 (m, 4H), 2.45 (t, J=7.2 Hz, 2H), 2.31-2.15 (m, 2H), 1.97-1.87 (m, 2H). MS [M+H]⁺ m/z 335.
BDM_70716

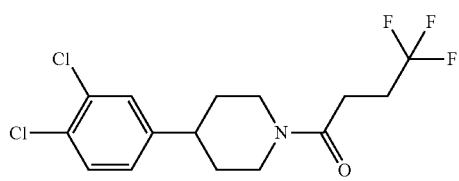 [SMILES: O=C(CCC(F)(F)F)N1CCC(c2ccc(Cl)c(Cl)c2)CC1]

¹H NMR (CDCl₃) δ 7.39 (d, J=8.3 Hz, 1H), 7.29 (d, J=2.0 Hz, 1H), 7.04 (dd, J=8.3 Hz, J=2.0 Hz, 1H), 4.82-4.77 (m, 1H), 4.00-3.94 (m, 1H), 3.21-3.12 (m, 1H), 2.79-2.48 (m, 6H), 1.96-1.88 (m, 2H), 1.67-1.51 (m, 2H).
¹³C NMR (CDCl₃) δ 167.99, 145.10, 132.60, 130.58, 128.84, 127.11 (q, J=275 Hz), 126.11, 45.74, 42.40, 41.90, 33.48, 32.53, 29.69 (q, J=29 Hz), 25.95. MS [M+H]⁺ m/z 354.
BDM_70536

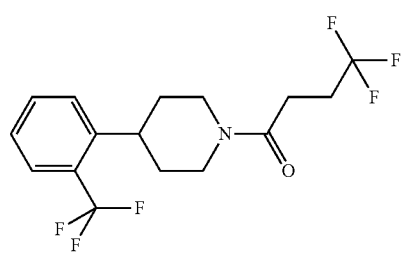 [SMILES: O=C(CCC(F)(F)F)N1CCC(c2ccccc2C(F)(F)F)CC1]

¹H NMR (CD₂Cl₂) δ 7.68 (d, J=4.5 Hz, 1H), 7.58 (t, J=4.5 Hz, 1H), 7.46 (d, J=4.5 Hz, 1H), 7.37 (t, J=4.5 Hz, 1H), 4.81-4.77 (m, 1H), 4.00-3.97 (m, 1H), 3.23-3.17 (m, 2H), 2.73-2.52 (m, 5H), 1.92-1.85 (m, 2H), 1.75-1.68 (m, 2H). MS [M+H]⁺ m/z 354.
BDM_70546

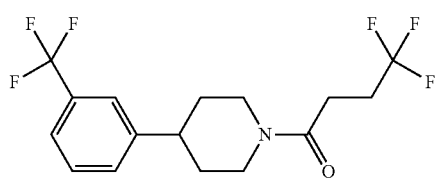 [SMILES: O=C(CCC(F)(F)F)N1CCC(c2cccc(C(F)(F)F)c2)CC1]

¹H NMR (CD₂Cl₂) δ 7.51-7.46 (m, 4H), 4.80-4.75 (m, 1H), 4.01-3.95 (m, 1H), 3.23-3.14 (m, 1H), 2.93-2.82 (m, 1H), 2.74-2.50 (m, 5H), 1.99-1.90 (m, 2H), 1.74-1.57 (m, 2H).
¹³C NMR (CD₂Cl₂) δ 167.72, 146.30, 130.56 (q, J=32 Hz), 130.37, 129.09, 127.44 (q, J=275 Hz), 124.35 (q, J=275 Hz), 123.51 (q, J=4 Hz), 123.25 (q, J=4 Hz), 45.73, 42.48, 42.29, 33.46, 32.63, 29.52 (q, J=28 Hz), 25.83. MS [M+H]⁺ m/z 354.
BDM_70667

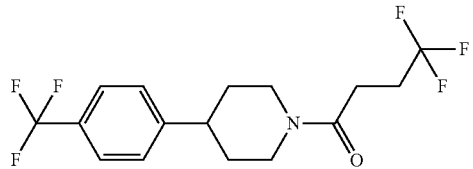 [SMILES: O=C(CCC(F)(F)F)N1CCC(c2ccc(C(F)(F)F)cc2)CC1]

¹H NMR (CD₂Cl₂) δ 7.61 (d, J=8.4 Hz, 2H), 7.37 (d, J=8.4 Hz, 2H), 4.80-4.74 (m, 1H), 4.01-3.95 (m, 1H), 3.23-3.13 (m, 1H), 2.92-2.82 (m, 1H), 2.73-2.48 (m, 5H), 1.98-1.89 (m, 2H), 1.73-1.61 (m, 2H). MS [M+H]⁺ m/z 354.
BDM_70665

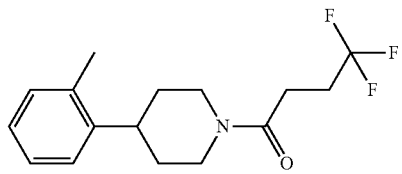 [SMILES: Cc1ccccc1C1CCN(C(=O)CCC(F)(F)F)CC1]

¹H NMR (CD₂Cl₂) δ 7.19-7.09 (m, 4H), 4.80-4.74 (m, 1H), 4.00-3.94 (m, 1H), 3.23-3.14 (m, 1H), 3.06-2.95 (m, 1H), 2.74-2.47 (m, 5H), 2.38 (s, 3H), 1.88-1.80 (m, 2H), 1.71-1.54 (m, 2H). MS [M+H]⁺ m/z 300.
BDM_70664

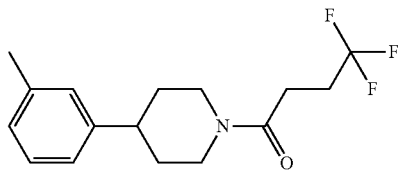 [SMILES: Cc1cccc(C2CCN(C(=O)CCC(F)(F)F)CC2)c1]

¹H NMR (CD₂Cl₂) δ 7.23-7.20 (m, 1H), 7.06-7.01 (m, 3H), 4.77-4.71 (m, 1H), 3.98-3.92 (m, 1H), 3.20-3.11 (m, 1H), 2.79-2.46 (m, 6H), 2.33 (s, 3H), 1.94-1.85 (m, 2H), 1.71-1.53 (m, 2H). MS [M+H]⁺ m/z 300.
BDM_70663

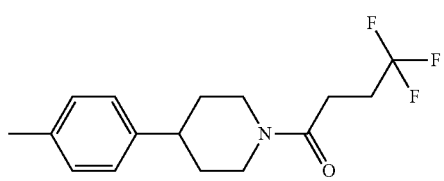 [SMILES: Cc1ccc(C2CCN(C(=O)CCC(F)(F)F)CC2)cc1]

¹H NMR (CD₂Cl₂) δ 7.16-7.10 (m, 4H), 4.77-4.70 (m, 1H), 3.97-3.91 (m, 1H), 3.20-3.10 (m, 1H), 3.06-2.95 (m,

1H), 2.77-2.47 (m, 5H), 2.33 (s, 3H), 1.93-1.85 (m, 2H), 1.69-1.51 (m, 2H). MS [M+H]⁺ m/z 300.
BDM_70540

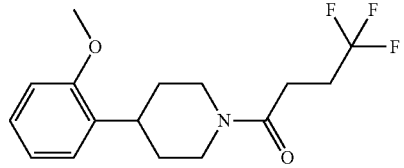 [SMILES: COc1ccccc1C1CCN(C(=O)CCC(F)(F)F)CC1]

¹H NMR (CD₂Cl₂) δ 7.25-7.15 (m, 2H), 6.98-6.91 (m, 2H), 4.78-4.72 (m, 1H), 3.97-3.92 (m, 1H), 3.86 (s, 3H), 3.28-3.14 (m, 2H), 2.75-2.47 (m, 5H), 1.94-1.84 (m, 2H), 1.69-1.54 (m, 2H).
¹³C NMR (CD₂Cl₂) δ 167.59, 156.89, 133.37, 127.49 (q, J=275 Hz), 127.18, 126.35, 120.56, 110.44, 55.23, 46.16, 42.73, 35.54, 32.31, 31.48, 29.59 (q, J=29 Hz), 25.81. MS [M+H]⁺ m/z 316.
BDM_70538

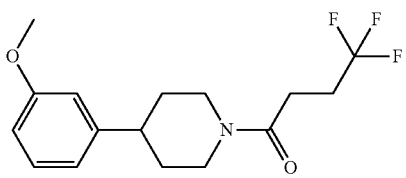 [SMILES: COc1cccc(C2CCN(C(=O)CCC(F)(F)F)CC2)c1]

¹H NMR (CD₂Cl₂) δ 7.27-7.22 (m, 1H), 6.83-6.76 (m, 3H), 4.78-4.71 (m, 1H), 3.99-3.92 (m, 1H), 3.80 (s, 3H), 3.20-3.11 (m, 1H), 2.81-2.47 (m, 6H), 1.95-1.87 (m, 2H), 1.71-1.54 (m, 2H). MS [M+H]⁺ m/z 316
BDM_70537

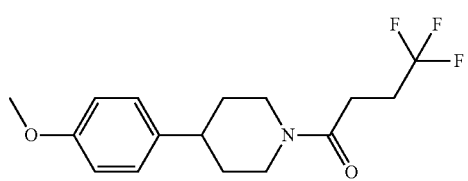 [SMILES: COc1ccc(C2CCN(C(=O)CCC(F)(F)F)CC2)cc1]

¹H NMR (CD₂Cl₂) δ 7.17-7.14 (m, 2H), 6.89-6.86 (m, 2H), 4.76-4.71 (m, 1H), 3.97-3.92 (m, 1H), 3.79 (s, 3H), 3.20-3.11 (m, 1H), 2.74-2.50 (m, 6H), 1.93-1.86 (m, 2H), 1.63-1.55 (m, 2H).
¹³C NMR (CD₂Cl₂) δ 168.38, 158.58, 138.06, 127.49 (q, J=275 Hz), 127.56, 113.81, 55.16, 45.97, 42.53, 41.76, 34.06, 33.12, 29.56 (q, J=29 Hz), 25.80. MS [M+H]⁺ m/z 316.
BDM_70539

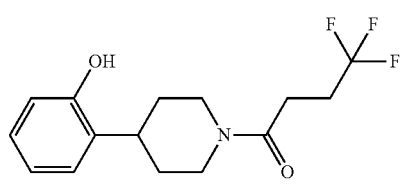 [SMILES: O=C(CCC(F)(F)F)N1CCC(c2ccccc2O)CC1]

¹H NMR (MeOD) δ 7.08 (dd, J=7.6 Hz, J=1.5 Hz, 1H), 7.00 (td, J=7.6 Hz, J=1.7 Hz, 1H), 6.80-6.74 (m, 2H), 4.71-4.64 (m, 1H), 4.09-4.02 (m, 1H), 3.27-3.15 (m, 2H), 2.80-2.70 (m, 3H), 2.58-2.47 (m, 2H), 1.96-1.83 (m, 2H), 1.74-1.53 (m, 2H). MS [M+H]⁺ m/z 302.
BDM_45572

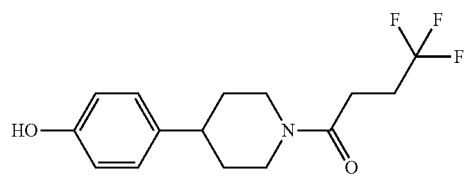 [SMILES: O=C(CCC(F)(F)F)N1CCC(c2ccc(O)cc2)CC1]

¹H NMR (MeOD) δ 7.04 (d, J=8.7 Hz, 2H), 6.72 (d, J=8.7 Hz, 2H), 4.67-4.61 (m, 1H), 4.04-3.98 (m, 1H), 3.21-3.12 (m, 1H), 2.75-2.66 (m, 4H), 2.58-2.46 (m, 2H), 1.89-1.79 (m, 2H), 1.67-1.44 (m, 2H). MS [M+H]⁺ m/z 302.
BDM_70542

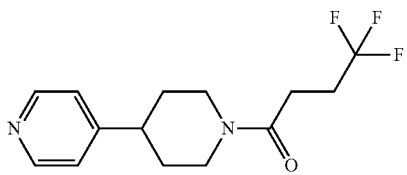 [SMILES: O=C(CCC(F)(F)F)N1CCC(c2ccncc2)CC1]

¹H NMR (CD₂Cl₂) δ 8.52 (d, J=6.1 Hz, 2H), 7.16 (d, J=6.1 Hz, 2H), 4.80-4.73 (m, 1H), 4.01-3.93 (m, 1H), 3.22-3.13 (m, 1H), 2.84-2.48 (m, 6H), 1.98-1.89 (m, 2H), 1.71-1.54 (m, 2H). MS [M+H]⁺ m/z 287.
BDM_70670

4-benzylpiperidine is commercially available. Only the coupling was performed.

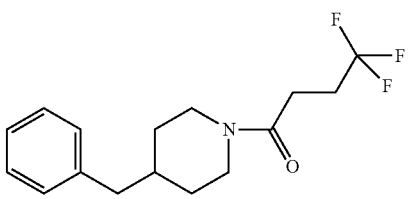 [SMILES: O=C(CCC(F)(F)F)N1CCC(Cc2ccccc2)CC1]

¹H NMR (CD₂Cl₂) δ 7.33-7.28 (m, 2H), 7.24-7.16 (m, 3H), 4.59-4.51 (m, 1H), 3.82-3.77 (m, 1H), 3.02-2.92 (m, 1H), 2.59-2.47 (m, 7H), 1.85-1.67 (m, 3H), 1.24-1.07 (m, 2H).

MS [M+H]⁺ m/z 300. BDM_70719

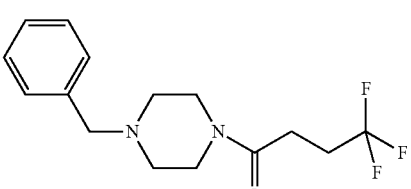

¹H NMR (CD₂Cl₂) δ 7.35-7.26 (m, 5H), 3.61 (t, J=5.1 Hz, 2H), 3.54 (s, 2H), 3.45 (t, J=5.1 Hz, 2H), 2.61-2.41 (m, 8H). MS [M+H]⁺ m/z 301.

BDM_70717

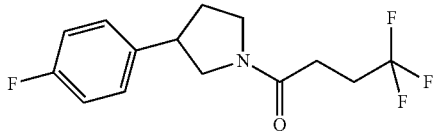 [SMILES: O=C(CCC(F)(F)F)N1CCC(c2ccc(F)cc2)C1]

¹H NMR (CDCl₃) δ 7.24-7.18 (m, 2H), 7.07-7.00 (m, 2H), 4-09-3.99 (m, 0.5H), 3.91-3.81 (m, 1H), 3.72-3.64 (m, 0.5H), 3.60-3.31 (m, 3H), 2.61-2.50 (m, 4H), 2.46-2.27 (m, 1H), 2.16-1.95 (m, 1H). MS [M+H]⁺ m/z 290.

BDM_44810

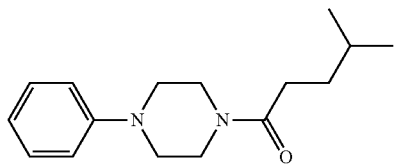 [SMILES: CC(C)CCC(=O)N1CCN(c2ccccc2)CC1]

¹H NMR (CDCl₃) δ 7.34-7.28 (m, 2H), 6.97-6.90 (m, 3H), 3.80 (t, J=5.1 Hz, 2H), 3.66 (t, J=5.1 Hz, 2H), 3.22-3.15 (m, 4H), 2.42-2.37 (m, 2H), 1.70-1.53 (m, 3H), 0.95 (d, J=6.3 Hz, 6H). MS [M+H]⁺ m/z 261.

BDM_44813

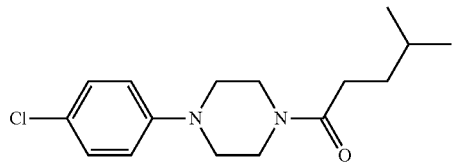

¹H NMR (CDCl₃) δ 7.26-7.22 (m, 2H), 6.91-6.86 (m, 2H), 3.74 (t, J=5.1 Hz, 2H), 3.63 (t, J=5.1 Hz, 2H), 3.18-3.11 (m, 4H), 2.39-2.34 (m, 2H), 1.67-1.49 (m, 3H), 0.95 (d, J=6.3 Hz, 6H). MS [M+H]⁺ m/z 295.

BDM_44821

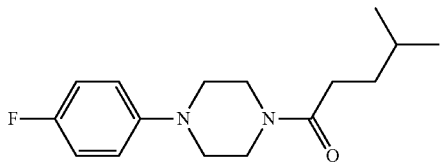 [SMILES: CC(C)CCC(=O)N1CCN(c2ccc(F)cc2)CC1]

¹H NMR (CDCl₃) δ 7.04-6.98 (m, 2H), 6.94-6.90 (m, 2H), 3.74 (t, J=5.1 Hz, 2H), 3.63 (t, J=5.1 Hz, 2H), 3.12-3.05 (m, 4H), 2.39-2.34 (m, 2H), 1.64-1.49 (m, 3H), 0.95 (d, J=6.6 Hz, 6H). MS [M+H]⁺ m/z 279.

BDM_44649

4-phenylpiperidine is commercially available. Only the coupling was performed.

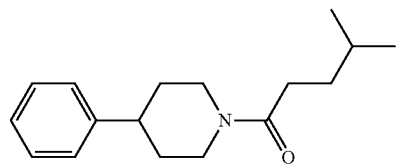 [SMILES: CC(C)CCC(=O)N1CCC(c2ccccc2)CC1]

¹H NMR (CD₂Cl₂) δ 7.36-7.31 (m, 2H), 7.25-7.20 (m, 3H), 4.77-4.73 (m, 1H), 4.02-3.98 (m, 1H), 3.18-3.09 (m, 1H), 2.81-2.71 (m, 1H), 2.66-2.57 (m, 1H), 2.39-2.34 (m, 2H), 1.94-1.85 (m, 2H), 1.69-1.51 (m, 5H), 0.95 (d, J=6.4 Hz, 6H). MS [M+H]⁺ m/z 260.

Evaluation of the Compounds' Activity

Potentiation of Ethionamide Cell Test

The test used made it possible to ascertain that these compounds were capable of potentiating the bactericide activity of ethionamide on *M. tuberculosis* alone. This test was a "High Content Screening" (HCS) or dense content screening test. HCS tests were performed on cell cultures that enable certain phenotypic features of a microorganism (e.g. a bacterium) in a given environment to be studied. The phenotypic changes observed can range from the increase (or decrease) of the production of certain marked proteins to the modification of the morphology of the microorganism under consideration. The method is described in the following publication: "Ethionamide Boosters: Synthesis, Biological Activity, and Structure-Activity Relationships of a Series of 1,2,4-Oxadiazole EthR Inhibitors", M. Flipo et al., Journal of Medicinal Chemistry, 2011, 54(8), 2994-3010.

This test aims to determine the ligand concentration necessary to potentiate ten times the activity of ethionamide (ETH).

To measure the ligand concentration necessary for potentiating ten times the activity of ETH, a constant concentration of ethionamide (0.1 μg/mL corresponding to 1/10 of its $CMI_{99}$) was chosen. By varying the ligand concentration, the concentration necessary to inhibit 50% of the bacterial growth, i.e. the concentration necessary to potentiate ten times the activity of ethionamide, was determined. This concentration was denoted $EC_{50}$.

Measurement of the Solubility

40 μL of a solution at 10 mM in DMSO of the sample was added to 1.96 mL MeOH or PBS at pH 7.4. The samples were then agitated during 24 h at RT, centrifuged during 5 min and then filtrated on filters of 0.45 μm size. 20 μL of each solution were then added to 180 μL MeOH and then analyzed by LC-MS. The solubility was determined as ratio of the surfaces of the mass signals PBS/MeOH.

Measured Biological Activities

The tables I to III hereafter summarize the formulas of the inventive compounds tested as well as the values of the $EC_{50}$ experimentally measured according to the aforementioned protocol.

TABLE I

| ID_structure | R2 | X | n | R1 | $EC_{50}$ (μM) | Solubility (μg/mL) |
|---|---|---|---|---|---|---|
| BDM_44647 | phenyl | CH | 1 | $CH_2CF_3$ | 0.0008 | 50.4 |
| BDM_44648 | phenyl | CH | 1 | $(CH_2)_2CF_3$ | <0.01 | 42.9 |

TABLE I-continued

| ID_structure | R2 | X | n | R1 | EC₅₀ (µM) | Solubility (µg/mL) |
|---|---|---|---|---|---|---|
| BDM_44751 | 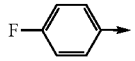 | CH | 1 | CH$_2$CF$_3$ | 0.001 | 51.9 |
| BDM_70717 | 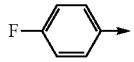 | CH | 0 | CH$_2$CF$_3$ | 0.009 | ND |

With reference to the results of Table I, one observes that a CH$_2$CF$_3$ group affords a greater potentiating activity of ethionamide without negatively affecting the compound's solubility. The results show that for a same radical R1 and a same radical R2, the potentiating activity of the inventive compounds was improved when n=1.

TABLE II

| ID_structure | R2 | X | n | R1 | EC₅₀ (µM) |
|---|---|---|---|---|---|
| BDM_44810 | 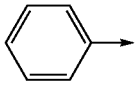 | N | 1 | (CH$_2$)isopropyl | 0.06 |
| BDM_44813 |  | N | 1 | (CH$_2$)isopropyl | 0.1 |
| BDM_44821 | 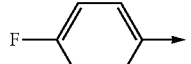 | N | 1 | (CH$_2$)isopropyl | 0.1 |
| BDM_44649 | 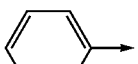 | CH | 1 | (CH$_2$)isopropyl | 0.06 |

Table III hereafter summarizes the activities expressed in EC$_{50}$ for all the inventive compounds tested.

TABLE III

| ID_structure | R2 | X | n | R1 | EC₅₀ (µM) |
|---|---|---|---|---|---|
| BDM_44647 |  | CH | 1 | CH$_2$CF$_3$ | 0.0008 |
| BDM_44648 | 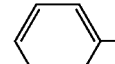 | CH | 1 | (CH$_2$)$_2$CF$_3$ | <0.01 |
| BDM_44649 | 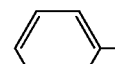 | CH | 1 | (CH$_2$)isopropyl | 0.06 |
| BDM_44808 | 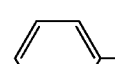 | N | 1 | CH$_2$CF$_3$ | 0.01 |
| BDM_44809 | 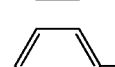 | N | 1 | (CH$_2$)$_2$CF$_3$ | 0.07 |

TABLE III-continued

| ID_structure | R2 | X | n | R1 | EC₅₀ (µM) |
|---|---|---|---|---|---|
| BDM_70666 | 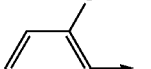 | CH | 1 | CH$_2$CF$_3$ | 0.001 |
| BDM_70531 | 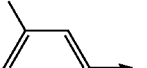 | CH | 1 | CH$_2$CF$_3$ | 0.0008 |
| BDM_44751 | 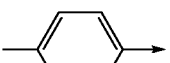 | CH | 1 | CH$_2$CF$_3$ | 0.001 |
| BDM_71148 | 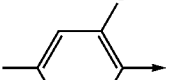 | CH | 1 | CH$_2$CF$_3$ | 0.001 |
| BDM_44819 | 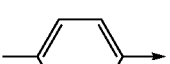 | N | 1 | CH$_2$CF$_3$ | 0.027 |
| BDM_44820 | 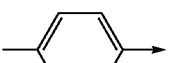 | N | 1 | (CH$_2$)$_2$CF$_3$ | 0.14 |
| BDM_70669 | 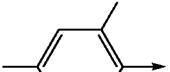 | N | 1 | CH$_2$CF$_3$ | 0.021 |
| BDM_70534 | 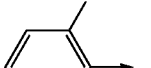 | CH | 1 | CH$_2$CF$_3$ | 0.11 |
| BDM_70668 | 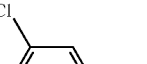 | CH | 1 | CH$_2$CF$_3$ | 0.0005 |
| BDM_70535 | 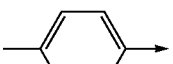 | CH | 1 | CH$_2$CF$_3$ | 0.12 |
| BDM_44811 |  | N | 1 | CH$_2$CF$_3$ | 0.010 |
| BDM_44812 |  | N | 1 | (CH$_2$)$_2$CF$_3$ | <0.02 |

TABLE III-continued

| ID_structure | R2 | X | n | R1 | EC$_{50}$ (μM) |
|---|---|---|---|---|---|
| BDM_70716 | 3,4-dichlorophenyl | CH | 1 | CH$_2$CF$_3$ | 0.025 |
| BDM_70536 | 2-CF$_3$-phenyl | CH | 1 | CH$_2$CF$_3$ | 0.770 |
| BDM_70546 | 3-CF$_3$-phenyl | CH | 1 | CH$_2$CF$_3$ | 0.001 |
| BDM_70667 | 4-CF$_3$-phenyl | CH | 1 | CH$_2$CF$_3$ | 0.3 |
| BDM_70665 | 2-methylphenyl | CH | 1 | CH$_2$CF$_3$ | 0.035 |
| BDM_70664 | 3-methylphenyl | CH | 1 | CH$_2$CF$_3$ | 0.001 |
| BDM_70663 | 4-methylphenyl | CH | 1 | CH$_2$CF$_3$ | 0.026 |
| BDM_70540 | 2-methoxyphenyl | CH | 1 | CH$_2$CF$_3$ | 0.14 |
| BDM_70538 | 3-methoxyphenyl | CH | 1 | CH$_2$CF$_3$ | 0.14 |
| BDM_70537 | 4-methoxyphenyl | CH | 1 | CH$_2$CF$_3$ | 0.002 |
| BDM_70539 | 2-hydroxyphenyl | CH | 1 | CH$_2$CF$_3$ | ND |
| BDM_45572 | 4-hydroxyphenyl | CH | 1 | CH$_2$CF$_3$ | 0.28 |
| BDM_70542 | 4-pyridyl | CH | 1 | CH$_2$CF$_3$ | 0.33 |
| BDM_70670 | benzyl | CH | 1 | CH$_2$CF$_3$ | 0.054 |
| BDM_70719 | benzyl | N | 1 | CH$_2$CF$_3$ | 1.1 |
| BDM_44810 | phenyl | N | 1 | (CH$_2$)isopropyl | 0.06 |
| BDM_44813 | 4-chlorophenyl | N | 1 | (CH$_2$)isopropyl | 0.1 |
| BDM_44821 | 4-fluorophenyl | N | 1 | (CH$_2$)isopropyl | 0.1 |
| BDM_70717 | 4-fluorophenyl | CH | 0 | CH$_2$CF$_3$ | 0.009 |

The invention claimed is:

1. A compound of formula (I):

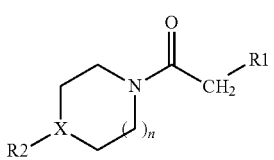

in which:
n is 0 or 1;
R1 is selected from the group consisting of —CH$_2$CF$_3$ and —CH$_2$CH$_2$CF$_3$;
X is N or CH;
R2 is selected from the group consisting of phenyl, benzyl, phenyl substituted by linear or branched C1-C4 alkyl, benzyl substituted by linear or branched C1-C4 alkyl, phenyl substituted by linear or branched C1-C4 alkyl substituted by fluorine, benzyl substituted by linear or branched C1-C4 alkyl substituted by fluorine, phenyl substituted by one or more substituent selected from Cl, F, CF$_3$, OCH$_3$, and OH, and a six-membered heterocycle comprising one, two or three nitrogen atoms.

2. The compound according to claim 1, wherein n is 1.
3. The compound according to claim 1, wherein R1 is —CH$_2$CF$_3$.
4. The compound according to claim 1, wherein X is CH.
5. The compound according to claim 1, wherein R2 is phenyl or benzyl.

6. The compound according to claim 1, wherein R2 is phenyl substituted in meta position relative to the bond to X by a substituent selected from Cl, F, CF$_3$ and OCH$_3$.

7. The compound according to claim 1, wherein R2 is phenyl substituted by fluorine.

8. The compound according to claim 1, wherein R2 is phenyl substituted by fluorine in para position relative to the bond to X.

9. The compound according to claim 1, wherein R2 is selected from:

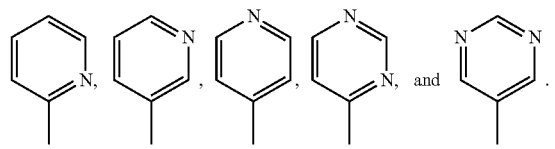

10. The compound according to claim 1, which is selected from the group consisting of:

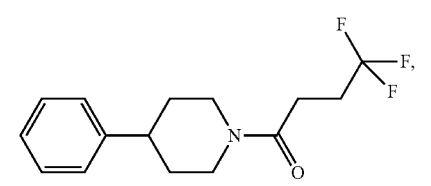

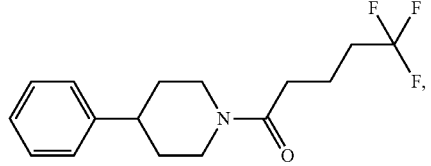

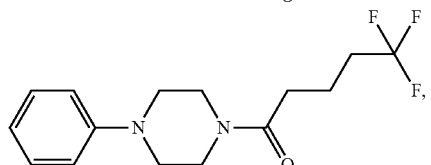

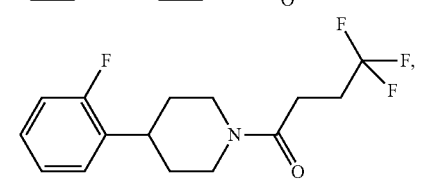

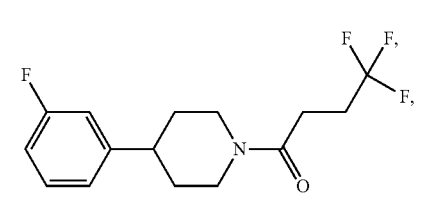

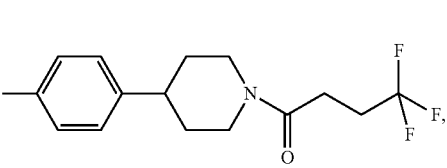

-continued

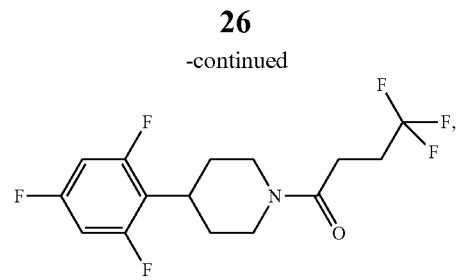

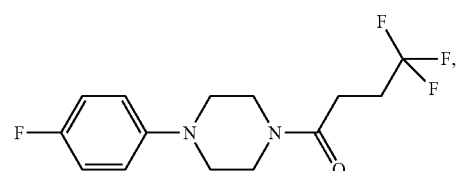

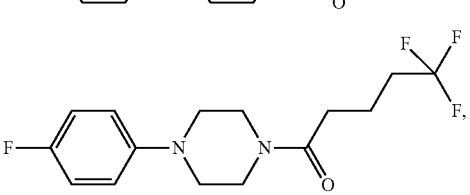

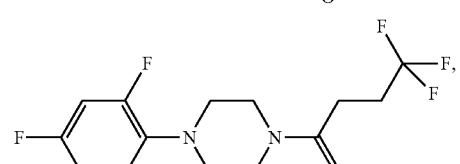

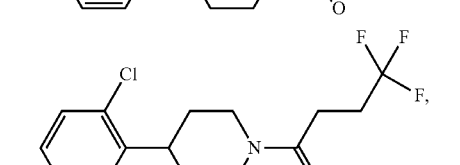

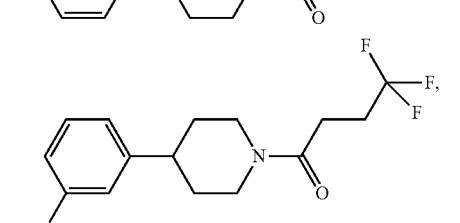

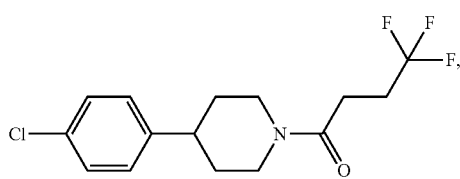

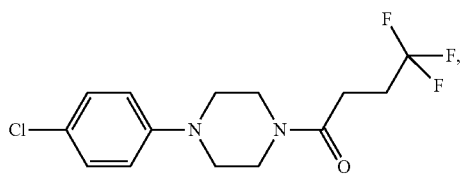

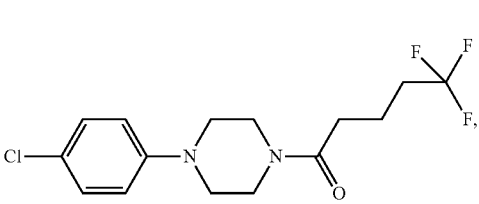

-continued

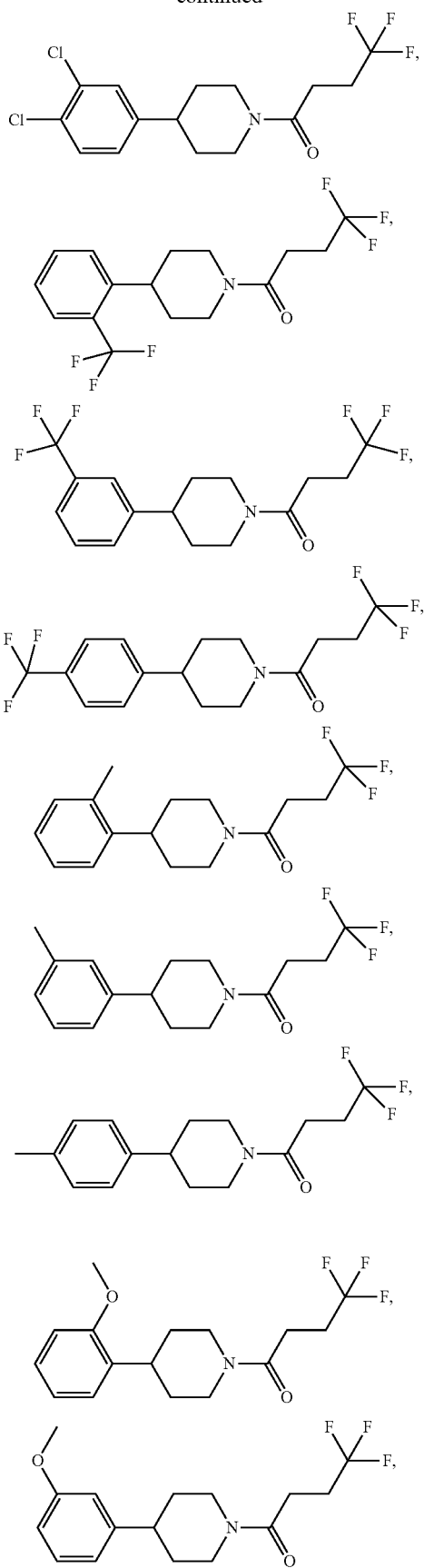

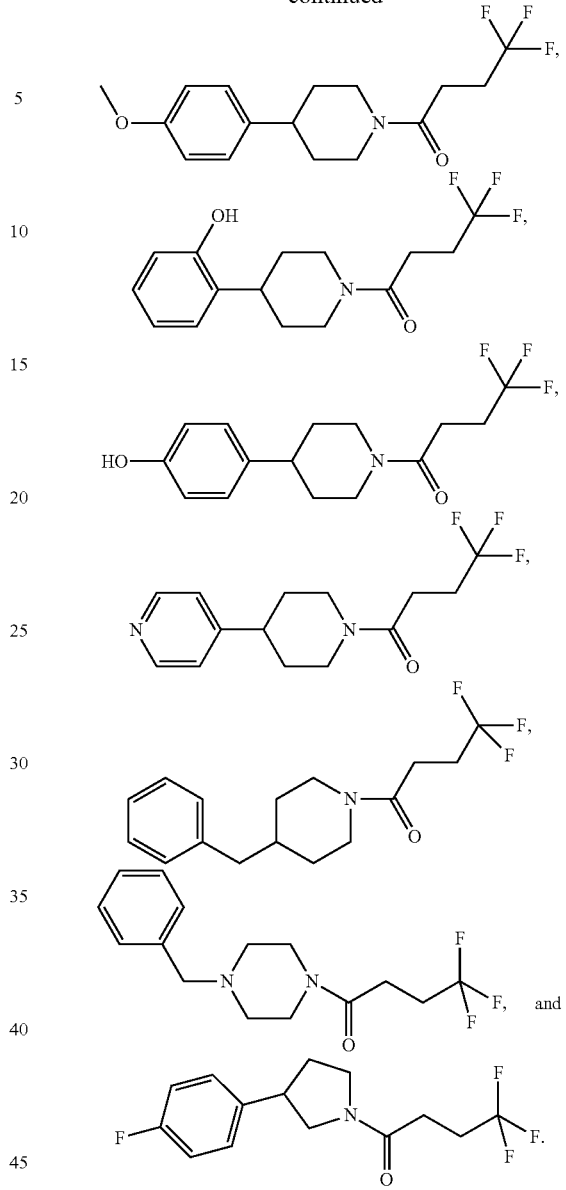

11. A method of treatment of tuberculosis, leprosy and atypical mycobacterial infections comprising administering to a patient in need thereof an effective amount of a compound of claim 1.

12. A pharmaceutical composition comprising as active ingredient a compound of claim 1 and a pharmaceutically acceptable excipient.

13. The pharmaceutical composition of claim 12 further comprising an antibiotic active against bacteria and/or mycobacteria.

14. The pharmaceutical composition of claim 12 further comprising an antibiotic activatable via the EthA pathway.

15. The pharmaceutical composition of claim 12 further comprising an antibiotic selected from the thioamide family.

16. The pharmaceutical composition of claim 12 further comprising ethionamide or prothionamide.

17. A method of treatment of tuberculosis, leprosy and atypical mycobacterial infections comprising administering to a patient in need thereof an effective amount of a compound of claim 1 and an effective amount of an antibiotic activatable via the EthA pathway.

18. A method of treatment of mycobacterial infections comprising administering to a patient in need thereof an effective amount of claim 1.

19. The compound according to claim 3, wherein n is 1.

20. The compound according to claim 19, wherein X is CH.

\* \* \* \* \*